United States Patent [19]

Huthmacher et al.

[11] Patent Number: 5,283,366
[45] Date of Patent: Feb. 1, 1994

[54] METHOD OF PREPARING 3-AMINOMETHYL-3,5,5-TRIMETHYL CYCLOHEXYL AMINE

[75] Inventors: Klaus Huthmacher, Gelnhausen; Hermann Schmitt, Rodenbach, both of Fed. Rep. of Germany

[73] Assignee: Degussa AG, Fed. Rep. of Germany

[21] Appl. No.: 22,852

[22] Filed: Feb. 25, 1993

Related U.S. Application Data

[63] Continuation of Ser. No. 841,010, Feb. 25, 1992, abandoned.

[30] Foreign Application Priority Data

Mar. 5, 1991 [DE] Fed. Rep. of Germany ....... 4106882

[51] Int. Cl.$^5$ ................ C07C 209/22; C07C 209/48
[52] U.S. Cl. ................................ 564/446; 564/448; 564/455
[58] Field of Search ............... 558/430; 564/445, 446, 564/448, 455, 490

[56] References Cited

U.S. PATENT DOCUMENTS

| | | | |
|---|---|---|---|
| 4,429,157 | 1/1984 | Disteldorf et al. | 564/446 |
| 4,647,701 | 3/1987 | Gibson | 564/480 |

FOREIGN PATENT DOCUMENTS

| | | |
|---|---|---|
| 0042119 | 12/1981 | European Pat. Off. |
| 394967 | 10/1990 | European Pat. Off. |
| 394968 | 10/1990 | European Pat. Off. |
| 3011656 | 10/1981 | Fed. Rep. of Germany |
| 123154 | 6/1987 | Japan |
| 972010 | 10/1964 | United Kingdom |

Primary Examiner—Richard L. Raymond
Assistant Examiner—Scott C. Rand
Attorney, Agent, or Firm—Cushman, Darby & Cushman

[57] ABSTRACT

The reductive amination of 1,3,3-trimethyl-5-oxocyclohexane carbonitrile (IPN) with ammonia and hydrogen in the presence of nickel- or cobalt Raney catalysts to 3-aminomethyl-3,5,5-trimethyl-cyclohexyl amine is achieved in a single stage with a good yield and requires no pressure distillation if a co-catalyst selected from the group consisting of salts of nickel, cobalt, yttrium, lanthanum and cerium is used in an amount of 0.01 to 0.5 mole per mole Raney catalyst.

9 Claims, No Drawings

METHOD OF PREPARING 3-AMINOMETHYL-3,5,5-TRIMETHYL CYCLOHEXYL AMINE

This is a continuation of application No. 07/841.010, filed on Feb. 25, 1992, which was abandoned upon the filing hereof.

The invention relates to a method of preparing 3-aminomethyl-3, 5,5-trimethylcyclohexyl amine by the reductive amination of 1,3,3-trimethyl-5-oxocyclohexane carbonitrile with ammonia and hydrogen using a nickel or cobalt Raney catalyst.

BACKGROUND OF THE INVENTION 3-aminomethyl-3,5,5-trimethylcyclohexyl amine, designated in the following as isophorone diamine, is used as a starting material for the preparation of isophorone diisocycanate, as an amine component for making polyamides and as a hardener for epoxide resins.

Isophorone diamine (IPDA) has been obtained in the past by the reductive amination of 1,3,3-trimethyl-5-oxocyclohexane carbonitrile, designated herein as "isophorone nitrile" (IPN), in the presence of ammonia and conventional hydrogenation catalysts. The isophorone nitrile used as a starting material can be obtained by means of the addition of hydrogen cyanide to isophorone - see German patent application P 39 42 371.9 (cf. Canadian Patent 2,032,667).

German patent DE 12 29 078, discloses using ammonia and IPN in a molar ratio of 10-30:1 in order to obtain IPDA. However, a rather large amount of by-products are produced in addition to the desired IPDA, such as in particular 3-aminomethyl-3,5,5-trimethylcyclohexanol (also known as isophorone amino alcohol (IPAA)), 1,3,3-trimethyl-6-azabicyclo-(3,2,1) octane and dihydroisophoryl amine. A yield of up to 81.4% IPDA is disclosed by way of example; however, there is no purity data. The cited yield proved to be non-reproducible, as has been determined by various parties.

In an attempt to obtain a high yield of IPDA and to minimize the undesired accumulation of IPAA, the method of German patent DE 12 29 078 was modified in accordance with the disclosure of published German patent application DE-OS 30 11 656 in such a manner that IPN was converted free of catalyst in a first stage with excess ammonia into 1,3,3-trimethyl-5-iminocyclohexane carbonitrile and the latter was hydrogenated in a second stage to IPDA. A considerable excess of ammonia had to be used in the second stage. This method of operation requires an expensive pressure distillation for recovery and recycling of the ammonia. According to the example given, a reaction yield of only 83.7% was achieved in the method of DE-OS 30 11 656 in spite of using a ratio of approximately 5 kg ammonia per 1 kg IPN; no data was supplied about the yield of isolated IPDA and its purity.

Published German patent application DE-OS 30 21 955 (cf. U.S. Pat. No. 4,429,157) makes it clear that there was a need to improve the methods of the previously cited documents. According to reference Example 1 of DE-OS 30 21 955, an IPDA yield of only 48% is achieved, in spite of an IPN/NH3 volumetric ratio of 1 to 10, in a method carried out by analogy with German patent DE 12 29 078. An unspecified "commercially available catalyst" was used in this instance. According to reference Examples 2 and 3 of DE-OS 30 21 955, carried out by analogy with published German patent application DE-OS 30 11 646, it was possible to obtain a yield of approximately 70% and 90%; however, a long reaction time was required for the first stage and an IPN/NH3 volumetric ration of 1 to 10 in the second stage was necessary for this. Thus, in addition to the disadvantage of the high ammonia excess, there is also an economically significant reduction of the space-time yield.

Published German Patent Application DE-OS 30 21 955 discloses that it is possible to reduce the long reaction time for the first stage—imine formation—in the method of DE-OS 30 11 656 by using an imine-formation catalyst. However, this increased the cost of the reaction, in addition, it still was necessary to use a very high ammonia/IPN volumetric ratio.

In the methods of DE-OS 30 11 656 and DE-OS 30 21 955, carrier-free or carrier-bound Co-, Ni-, Fe- and noble metal catalysts, among others also Raney nickel and Raney cobalt, are designated as suitable. A possible co-use of catalytic amounts of acids and ammonium salts is referred to in DE-OS 30 11 656 but without disclosing details about the type of material to use.

Published Japanese Patent Application JP-A-62-123154 discloses a method for the reductive amination of IPN for the preparation of IPDA in which an attempt is made to reduce the required excess of ammonia and to eliminate the preliminary reduction of the carrier-bound catalyst. According to this method, it should be possible to obtain IPDA in high yield—yields between 83 and 89% in the reaction mixture are indicated in the examples—if a 1 to 20-fold, preferably 5 to 10-fold molar amount of ammonia is used, relative to IPN, as well as Raney cobalt as catalyst, a pressure of 50 to 150 bars and a temperature of 50° to 150° C.

By reworking the method of JP-A 62-123154, it has been determined that, in spite of increasing of the excess of ammonia over the value indicated in the Japanese document, almost no absorption of hydrogen took place and Raney cobalt alone is therefore practically ineffective.

SUMMARY OF THE INVENTION

The object of the present invention is to improve the method of preparing isophorone diamine from isophorone nitrile in such a manner that IPDA can be obtained in good yield even with the readily available Raney catalysts. A further object is to carry out the reductive amination in the presence of a small enough excess of ammonia that pressure distillation is not necessary.

These and other objects are achieved in a method of preparing 3-aminomethyl-3,5,5-trimethylcyclohexyl amine by reductive amination of 1,3,3-trimethyl-5-oxocyclohexane carbonitrile (IPN) with ammonia and hydrogen at a pressure of 5 to 20 MPa and a temperature of 50° to 150° C. using a nickel or cobalt Raney catalyst and in the presence of an organic solvent in which a co-catalyst selected from the group consisting of salts of nickel, cobalt, yttrium, lanthanum and cerium is used in an amount of 0.01 to 0.5 mole per mole Raney catalyst.

According to the invention, Raney nickel catalysts and Raney cobalt catalysts can be used; Ni and Co Raney catalysts which can be doped with other metals such as especially Mn and Fe are also useful. The Raney catalysts can be obtained in a known manner from alloys of nickel or cobalt with aluminum and/or Zn, Mg, Si, as well as optionally the doping elements, by leaching out the aluminum or the Zn, Mg or Si. In most instances, the leaching is carried out with alkaline materials.

The use of co-catalysts is essential for the invention. Salts of Ni, Co, Y, La, Ce, especially of Ni and Co, are preferred. The anion of these salts can be the anion derived from mineral acids, especially sulfuric acid and hydrochloric acid. Anions derived from carboxylic acids may also be used. Halides, especially chlorides, of the cited metals, are especially useful.

The amount of co-catalysts used can be within broad limits. It is advantageous to use 0.01 to 0.5 mole, especially 0.05 to 0.2 mole, co-catalyst per mole Raney catalyst, calculated as Co or Ni. The salts can be supplied to the hydrogenation batch as anhydrous salts or salts containing water of crystallization, in powder form or as a solution or suspension.

The hydrogenation can be carried out in the presence of ammonia. It is advantageous to add 0.25 to 2.5 kg $NH_3$, especially 0.5 to 1 kg $NH_3$, per kg isophorone nitrile, to the reaction batch e.g. by pressing on liquid ammonia.

Finally, an organic solvent or mixture of organic solvents are used in the reaction mixture. Solvents which can be used are those which have sufficient solvent power for IPN and IPDA at the hydrogenation temperature, so that these substances are present in dissolved form at that temperature. The following are suitable, for example: Lower alcohols, especially monovalent $C_1$ to $C_4$ alcohols, aliphatic and cycloaliphatic mono- and diethers, especially those with up to 6 carbon atoms, as well as hydrocarbons in general such as e.g. cyclohexane and toluene. These solvents are preferred which have a boiling point below 120° C. and can be readily distilled from the reaction mixture after completion of the hydrogenation.

The reductive amination is carried out at a pressure in the range of 5 to 20 MPa, especially 10 to 15 MPa. Hydrogen is supplied under pressure to the IPN, ammonia, solvent catalyst and co-catalyst in a pressure reactor until the desired pressure is achieved; the pressure is preferably maintained during the hydrogenation by supplying hydrogen. The hydrogenation temperature is 50° to 150° C., preferably 80° to 130° C.

The hydrogenation can be carried out discontinuously or continuously and conventional hydrogenation reactors such as those employed for hydrogenations using suspension catalysts can be used. Agitation autoclaves and loop-type bubble reactors may be mentioned by way of example. The workup of the reaction mixture, after the completion of the hydrogenation, may be carried out in a known manner. Conventional steps include the release of pressure, evaporating the ammonia, separation of the insoluble components from the solution, separation of the solvent by means of distillation and the fractional distillation of crude IPDA under reduced pressure.

It was surprisingly found that, by using the cocatalysts of the invention, it is possible to use Raney Co and Raney Ni catalysts for the efficient reductive amination of isophorone nitrile to isophorone diamine. The method can be carried out in a simple manner; as a rule, a pressure distillation is not necessary.

DETAILED DESCRIPTION OF PREFERRED EMBODIMENTS

The invention is illustrated by the following examples.

EXAMPLE 1

400 g (2.42 moles) isophorone nitrile are dissolved in a 5 liter autoclave with a gassing agitator in 1 liter methanol and 1 liter of anhydrous ammonia. After the addition of 100 g Raney cobalt (containing approximately 25% water) and 50 g cobalt chloride hexahydrate as catalyst, the mixture is agitated at 1200 rpms and hydrogen is introduced until the pressure reaches 130 bars. Hydrogen absorption takes place upon heating to 80° C.; the temperature is raised to 130° C. toward the end of the hydrogenation. The total reaction time is 3-4 hours. After the mixture has cooled off, the catalyst is filtered off and the excess ammonia and the methanol distilled off; the residue is distilled in a vacuum.

| First runnings: | 12 g $bp_{0.1}$: 30–65° C. |
|---|---|
| Main fraction (IPDA): | 350 g $bp_{0.1}$: 65–68° C. |
| Residue: | 13.2 g |
| Yield: | 85.0% of theory IPDA (rel. to IPN) |
| Product purity (GC): | approximately 98% |

EXAMPLE 2

The process of Example 1 is repeated; however, 1.5 liters methanol and 1.5 liters anhydrous ammonia are used (instead of 1 liter of each). The yield of IPDA is 351 g (=85.3% of theory).

EXAMPLE 3

The process of Example 1 is repeated, but with 500 g (3.30 moles) isophorone nitrile and only 0.5 liter anhydrous ammonia.

Yield: 345.1 g (67.0% of theory) IPDA

Residue contains salt: IPDA ×½ HCl

After liberating the free base with sodium hydroxide solution, it was possible to isolate a total of 396.6 g (77% of theory) of IPDA.

REFERENCE EXAMPLE

The procedure of Example 2 was repeated, but without cobalt chloride hexahydrate as co-catalyst. Almost no hydrogen is absorbed. There was no isolatable yield.

What is claimed is:

1. In a method of preparing 3-aminomethyl-3,5,5-trimethylcyclohexyl amine by reductive amination of 1,3,3-trimethyl-5-oxo-cyclohexane carbonitrile (IPN) with ammonia and hydrogen at a pressure of 5 to 20 MPa and a temperature of 50° to 150° C. using a nickel or cobalt Raney catalyst and in the presence of an organic solvent; the improvement which comprises carrying out the reaction in the presence of a co-catalyst selected from the group consisting of salts of nickel and cobalt in an amount of 0.05 to 0.5 mole per mole of Raney catalyst.

2. The method of claim 1 in which the co-catalyst is an anydrous salt or a salt containing water of crystallization, said salt being a salt of a mineral acid.

3. A method as set forth in claim 2 in which said mineral acid is sulfuric acid or hydrochloric acid.

4. The method of claim 1 or 2 in which the co-catalyst is a halide.

5. A method as set forth in claim 4 in which the co-catalyst is a chloride.

6. A method as set forth in claim 1 or claim 2 in which the Raney catalyst and the co-catalyst are used in a molar ratio of 1:0.05 to 0.2.

7. A method according to claim 1 or claim 2 in which 0.25 to 2.4 kg ammonia are used per kg IPN.

8. A method according to one claim 1 or claim 2 in which the hydrogenation is carried out at a pressure of 10 to 15 MPa and a temperature of 80° to 130° C.

9. In a method of preparing 3-aminomethyl-3, 5, 5-trimethylcyclohexyl amine by reductive amination of 1,3,3-trimethyl-5-oxo-cyclohexane carbonitrile (OPN) with ammonia and hydrogen at a pressure of 5 to 20 MPa and a temperature of 50° to 150° C. using a nickel or cobalt Raney catalyst and in the presence of an organic solvent;

the improvement which comprises carrying out the reaction in the presence of a cocatalyst selected from the group consisting of salt of nickel, cobalt, yttrium, lanthanum and cerium with an acid selected from the group consisting of mineral acids and carboxylic acids, in an amount of 0.01 to 0.5 mole per mole Raney catalyst.

* * * * *